United States Patent [19]

Lehrer

[11] Patent Number: 4,479,714
[45] Date of Patent: Oct. 30, 1984

[54] REFLECTION DENSITOMETER WITH ELLIPSOID REFLECTION SURFACE

[76] Inventor: Leo K. Lehrer, 1004 Berlin Rd., Cherry Hill, N.J. 08034

[21] Appl. No.: 254,191

[22] Filed: Apr. 14, 1981

[51] Int. Cl.³ .......................................... G01N 21/55
[52] U.S. Cl. .................................................. 356/445
[58] Field of Search ............... 356/445, 446, 338, 340, 356/447, 448, 339, 341, 342

[56] References Cited

U.S. PATENT DOCUMENTS

| 1,897,219 | 2/1933 | Schroter | 250/237 R |
| 3,010,358 | 11/1961 | Siegler, Jr. | 356/448 |
| 4,082,458 | 4/1978 | Fukui et al. | 356/445 |

FOREIGN PATENT DOCUMENTS

| 70732 | 5/1980 | Japan | 356/338 |
| 486251 | 1/1976 | U.S.S.R. | 356/338 |

Primary Examiner—Bruce Y. Arnold
Attorney, Agent, or Firm—Morton C. Jacobs

[57] ABSTRACT

A reflection densitometer includes an optical assembly formed with an ellipsoidal internal reflecting surface receiving light from a specimen at a target region located at one focus of the ellipsoidal surface and directing light to a photodetector at the other focus. A light source is mounted concentrically within the ellipsoidal surface, coaxially with the target and photodetector.

15 Claims, 3 Drawing Figures

REFLECTION DENSITOMETER WITH ELLIPSOID REFLECTION SURFACE

BACKGROUND OF THE INVENTION

This invention relates to densitometers and particularly to a reflection densitometer.

The measurement of reflection density is described, for example, in SPSE Handbook of Photographic Science and Engineering edited by W. Thomas, Jr. (John Wiley, 1972) at pages 839–40, and an optical system therefor is described at pages 857–858. A desirable feature of such densitometers is that it be highly compact, and for some purposes it should be a hand-held, self-contained instrument. With such restrictions, it is extremely desirable that the length of the optical system be very short; for example, desirably about 1" or less. When such a compact optical system is available, the lamp can be small and with a low energization requirement.

SUMMARY OF THE INVENTION

It is an object of this invention to provide a new and improved reflection densitometer.

Another object is to provide a new and improved reflection densitometer with a short optical system.

Another object of this invention is to provide a new and improved reflection densitometer which is highly efficient in transmitting light from a specimen at the target region to a light detector.

Another object of this invention is to provide a new and improved reflection densitometer which is compact, hand-held and portable.

In an embodiment of this invention, a reflection densitometer is constructed with an annular ring reflecting surface in which is mounted a lamp. A target finder is mounted on one side of the reflecting ring, and a photodetector on the other side of the reflection ring. The target and photodetector are each located at the two foci of an ellipse, and the reflection surface is formed as a segment of the ellipsoid of revolution of that ellipse. With this construction, an extremely efficient light coupling in the form of the highly polished ellipsoid surface is provided for efficiently transmitting light reflected from the target to the photodetector. Light from the target at one of the two foci of the ellipse is reflected to the other of the foci by the ellipsoid reflector.

The foregoing and other objects of this invention, the various features thereof, as well as the invention itself may be more fully understood from the following description when read together with the accompanying drawing, in which.

In the drawing, corresponding parts are referenced throughout by corresponding numbers.

Figure 1:
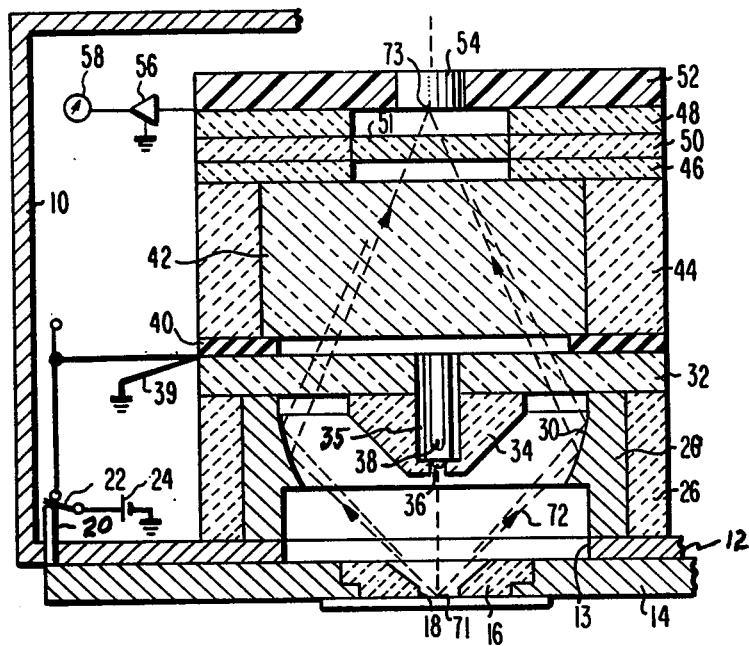
FIG. 1 is an enlarged cross-sectional view of a portion of a reflection densitometer embodying this invention and with some parts shown as a schematic diagram.
Figure 2:
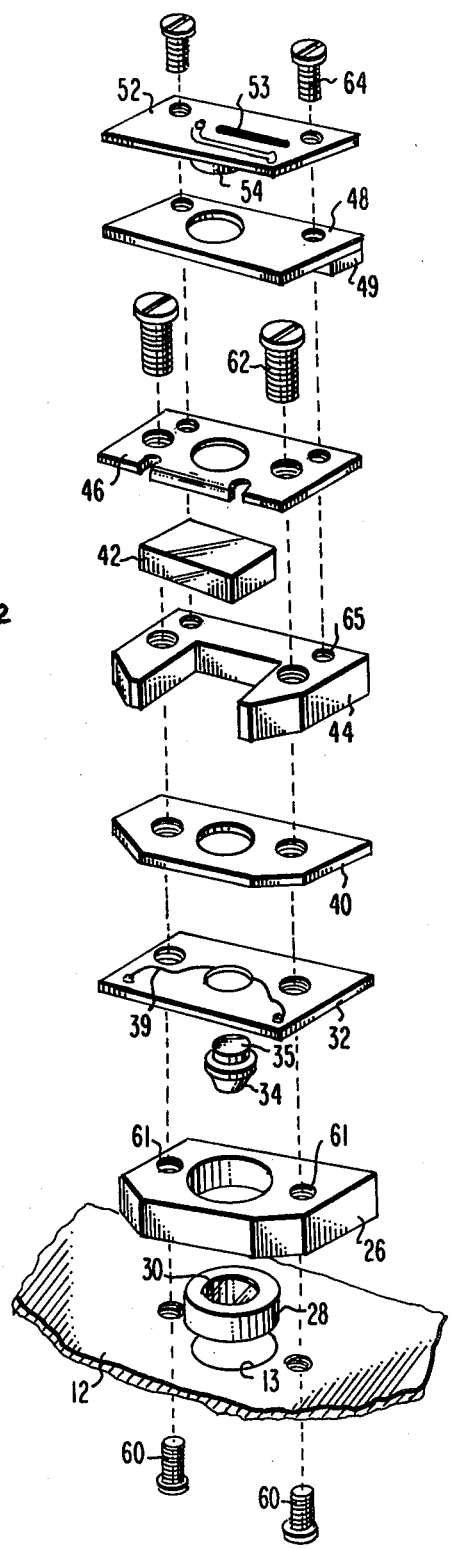
FIG. 2 is an exploded view of the optical assembly of FIG. 1.

The reflection densitometer of this invention as shown in the embodiment of FIGS. 1 and 2 is mounted in a portable, hand-held casing 10, and fixed to the lower wall plate thereof. Hinged to the lower wall 12 is finder plate 14 that contains an apertured, opaque target element 16, the aperture 18 of which fits over a region of the specimen 19, whose reflection density is to be measured. The aperture 18 of target 16 is conical to provide a generally conical path for the reflected light rays shown by broken lines 72.

The hinge plate 14 also has a pin 20 which passes through an aperture in the bottom wall of the casing and engages a microswitch 22 for completing the energization circuit from a battery 24 to the electrical portions of the densitometer. This hinge plate is spring-biased away from casing wall 12, so that the switch 22 is normally open. Upon locating the specimen area in target aperture 18 and pressing the casing down on the hinge plate 14, the pin 20 actuates switch 22 to initiate the measurement process.

Mounted within an opaque holder 26 is a circular reflection ring 28. The latter has a highly polished reflection surface 30 which extends all around the inside of the ring. Mounted on and fixed to the holder 26 is a transparent, thin illuminator window 32 made of plastic, and supported at the center thereof is a lamp holder 34 which is bonded to and depends from the window 32. The lamp holder 34 has a generally conical external shape which is concentric with the reflection ring 28. The lamp holder 34 has a central opening in which is located an electric lamp 35 having a lens 36 at the lower tip thereof. This lens is effective for concentrating the light from the lamp filament 38 at the target aperture 18. Back light from the lamp 35 is closed off by suitable black cement covering the lamp hole in window 32, and the cement also retains the lamp in position.

The electric lamp leads 39 extend through the illuminator window 32 and along the upper surface thereof between that window 32 and the rubber cushioning spacer 40 to soldered terminals at corners of window 32. Above the spacer cushion 40 is an infrared filter 42 held in an opaque U-shaped retainer 44 and held down by an opaque filter assembly plate 46 which has a downward projecting retainer lip depending from an edge thereof. The latter plate, together with another opaque filter assembly plate 48 (with a rear depending lip) support a filter frame 50 and apertures in those plates 46 and 48 and a filter aperture in the frame 50 are aligned. The filter 51 is appropriate for the specimen whose reflection density is to be measured, and filter frame 50 may have a plurality of such filters in adjacent apertures and be slidable transversely to position each one in alignment with the optical axis.

An opaque top retaining plate 52 carries a photodetector 54, as well as a printed circuit board that connects the detector output to a suitable amplifier and computer circuitry 56, the output of which is displayed upon a meter 58. All of the electrical circuitry is energized from battery 24 under control of the microswitch 22.

The reflecting-ring holder 26 has chamfered corners that permit the leads 39 of the lamp 35 to pass and connect to the circuitry 56 also assembled compactly in casing 10. The leads 39 from the lamp connect to terminals at the corners of the illuminator window. The reflecting ring 28 is press fit (and bonded if necessary) in the large central opening of the ring holder 26.

Assembly screws 60 pass through the lower casing wall 12 and into the lower portion of threaded holes 61 in ring holder 26 to fix that holder and its reflecting ring at the wall aperture 13. In addition, screws 62 pass through the side openings of filter holding plate 46, filter holder 44, spacer 40, illuminator window 32 and the upper portion of threaded holes 61 to affix that section of the optical assembly. In addition, the detector and printed circuit board 52 is retained by screws 64 in corner openings of the detector plate 52, filter assembly plate 48 and 46 and into the corner apertures 65 of the U-shaped filter holder 44. A photodiode has been found suitable as the photodetector.

In a reflection densitometer, the critical requirement for the collection optics is that the light energy reflected from the sample location be efficiently coupled to the detector. This should occur only within an angular aperture from 40 to 50 degrees. This forms a circular ring. The ring 28 is made to subtend that required angle. This physical ring is made to reflect all that reflection light energy to the photodetector. A highly effective optical assembly package is thereby produced which provides an accurate image at a magnification of low range (i.e., 1 to 5 times) and allows insertion of spectral filtering to fit various requirements for the graphic print, medical testing or other industries.

An ellipsoid of revolution has the property that any energy emitted at one focus of the ellipse is relayed by reflection to the other focus. If, indeed, the surface of the ellipsoid is made to provide specular reflection, the reflective coupling is made quite efficient. For this miniature reflection densitometer, the reflection-ring surface 30 is given an annular section from an ellipsoid of revolution. In order to improve the ease of fabrication and the ease of insertion of optics into the rear focus, which reduces the angular extent of the bundle of light passing to the detector, the ellipse is dimensioned to produce a magnification greater than 1. This is optimized to fit the sizes of the photodetector and specimen. This construction also ensures that the ellipsoid surface 30 is monotonically increasing in diameter over the length of the surface required for coupling from the lower to upper edge. The angle is made large enough to allow fabrication by a molding or replication technique.

Other rays are blocked from the detector by an opaque lamp housing and by other opaque members fabricated, for example, of carbon polycarbonate that define the annular light paths from specimen to reflector-ring 30 and from the ring to photodetector. The lamp housing aperture along with the lamp filament form a light source of the appropriate limited angular extent, and it is effectively suspended in the middle of the optics aperture using a transparent plastic plate. The lamp housing, lamp and plastic window plate form a simple, easily replaced lamp module.

The high precision ellipsoid reflecting surface on ring 28 is machined under computer control, and the deposit of the reflecting surface is formed by a replication process in which a ring of epoxy is transferred to form the inner ellipsoid surface 30. A male master is machined to the precise ellipsoid geometry, and deposited on this master is an ellipsoid ring of epoxy. That epoxy ring is then transferred as the inner ellipsoid surface 30 of the metal reflecting ring 28 and bonded thereto in the transfer process. Other types of techniques of lesser precision may be used for providing a reflecting coating on the ellipsoid ring; for example, by electroplating.

Figure 3:
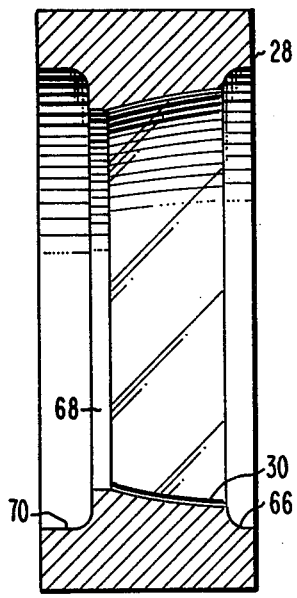
FIG. 3 is a further enlarged cross-sectional view of an ellipsoidal reflection ring used in the embodiment of FIG. 1.

Recesses 66, 68 and 70 (FIG. 3) formed in the openings on either side of the reflection ring 30 are used in mounting the reflection ring on a computerized lathe during fabrication, and in a suitable jig for the transfer of the epoxy surface 30 in the replication process.

In operation, when the hinge plate 14 is pressed down over a target at the target aperture 18, the switch pin 20 actuates the switch 22 and energizes the lamp filament 38. Light from the lamp (a small fraction of an inch long with a lens at the lower tip) is focused by that lens at the target aperture 18, at one focus of the ellipse. The reflected light from the specimen's target region passes through the space formed between the conical lamp holder 34 and the reflecting ring surface 30 as shown by the broken line rays 72.

The circuitry for the photodetector and measuring circuit 54, 56 and 58 are also energized with the lamp during operation. Light received by the photodetector 43 is reflected upward from the ellipsoid reflection ring surface 30, through the window 32, the axially aligned aperture in the spacer cushion 40, the infrared filter 42, and the apertures in filter support plates 46 and 48, and the filter 51 in the aperture in filter holder 50. Thus, this reflected light impinges on photodetector 54 at the other of the ellipse's foci. An electrical signal corresponding to the reflected light energy is produced and used for computing a measurement of the reflection density of the specimen.

In a particular embodiment of the invention developed for use in the graphic arts industry, a length of about three-fourths of an inch was used for the optical assembly from one ellipse focus to the other, in an arrangement, such as is shown in FIGS. 1 and 2. For example, the semi-major axis of the ellipse was about 0.4 inch, and the semi-minor axis about 0.25 inch, and the distance between foci about 0.7 inch. This compact assembly and short optical paths were achieved as a consequence of the use of the precision ellipsoidal reflecting surface in a short annular section.

Thus, a new and improved reflection densitometer is produced by this invention. Various modifications, in addition to those set forth above, will be apparent to those skilled in the art. This invention is intended to encompass such modifications, alternatives and equivalents as are included within the scope and spirit of the invention defined in the following claims.

What is claimed is:

1. A reflection densitometer comprising:
means defining a target region for a specimen whose reflection density is to be measured;
means for directing light to said target region;
electric means for detecting light reflected from a specimen at said target region and for producing a signal proportional to the reflection density of the specimen;
and means for reflecting said light reflected from said target region to said light detecting means;
said light reflecting means including an annular ellipsoidal light reflecting surface, and said electric means and said target region being respectively located at the foci of said ellipsoidal surface;
said light directing means including a source of light in an opaque holder located inside said annular ellipsoidal surface, said light directing means and said electric means being located, together with said target region, on the axis of said ellipsoidal surface,
so that a compact optical assembly of about one inch thickness extends between said target region and said light detecting means.

2. A reflection densitometer as set forth in claim 1 wherein said opaque holder for said light source is conically shaped and located concentrically with, and spaced from, said ellipsoidal surface, a light path being formed between said opaque holder and said ellipsoidal surface.

3. A reflection densitometer as set forth in claim 2 wherein said light path forms an annular space to said ellipsoid surface, said ellipsoid surface subtending an angle of about 40°–50° from said target.

4. A reflection densitometer as set forth in claim 1 wherein said light source includes an electric lamp and focusing lens for directing light to said target region.

5. A reflection densitometer as set forth in claim 1 wherein said electric means includes means for calculating reflection density from a signal produced by said light detecting means, and includes means for producing an output indication of the calculated reflection density.

6. A reflection densitometer as set forth in claim 5 wherein said target region defining means includes a plate hinged to the casing in which said optical assembly is located, said hinged plate having a projecting portion extending into said casing when said plate is hinged closed and located between said casing and a specimen; said light detecting means including switch means for supplying energization for said light detecting means and said calculating means, said switch being engageable by said hinged plate projection to be actuated thereby.

7. A reflection densitometer comprising:
means defining a target region for a specimen whose reflection density is to be measured;
means including a lamp for directing light to said target region;
electric means spaced about one inch from said target for detecting light reflected from a specimen at said target region, and for producing a signal proportional to the reflection density of the specimen; and means for reflecting light from said target region to said light detecting means;
said light reflecting means including an annular ellipsoidal light reflecting surface, and said light detecting means and said target region being respectively located at the two foci of said ellipsoid, said annular reflecting surface having a monotonically changing diameter in the direction from the target to the detector
so that a compact optical assembly extends between said target region and said light detecting means.

8. A reflection densitometer as set forth in claim 7 wherein said light reflecting means includes an annular metallic ring with said ellipsoidal light reflecting surface formed internally thereon.

9. A reflection densitometer as set forth in claim 8 wherein said ellipsoidal surface further includes a highly reflecting epoxy layer deposit on the inside of said annular ring.

10. A reflection densitometer as set forth in claim 7 wherein the light path between said annular reflector and said detecting means includes an infrared filter.

11. A reflection densitometer as set forth in claim 10 wherein said light path between said annular reflector and said detecting means further includes a holder for positioning a color filter therein.

12. A reflection densitometer as recited in claim 7 wherein said lamp is located along the axis of said ellipsoidal reflecting surface and closer to said target defining means than to said light detecting means.

13. A reflection densitometer as recited in claim 12 wherein said ellipsoidal surface surrounds said lamp.

14. A reflection densitometer as recited in claim 7, wherein an infrared filter is located between said light detecting means on one side and said reflecting means on the other side.

15. A reflection densitometer comprising:
means defining a target region for a specimen whose reflection density is to be measured;
means for directing light to said target region;
electric means for detecting light reflected from a specimen at said target region, and for producing a signal proportional to the reflection density of the specimen; and
means for reflecting light from said target region to said light detecting means;
said light reflecting means including an annular ellipsoidal light reflecting surface, and said light detecting means and said target region being respectively located at the two foci of said ellipsoid, said annular reflecting surface subtending a substantial and small acute angle from said target region so that a compact optical assembly of about one inch extends between said target region and said light detecting means;
the ellipsoid of said annular reflecting surface being structured to produce a magnification greater than one and its diameter being monotonically increasing in the direction from the target to the detector.

* * * * *